(12) United States Patent
Liu et al.

(10) Patent No.: US 10,947,179 B2
(45) Date of Patent: Mar. 16, 2021

(54) 2-(3,4-DIHYDROXYPHENYL)ETHYL 3-HYDROXYBUTANOATE, COMPOSITION, AND METHOD FOR IMPROVING FUNCTION OF AORTIC ENDOTHELIAL CELL

(71) Applicant: XI'AN JIAOTONG UNIVERSITY, Xi'an (CN)

(72) Inventors: Jian-Kang Liu, Xi'an (CN); Xu-Yun Liu, Xi'an (CN); Ya-Chong Hu, Xi'an (CN); Lin Zhao, Xi'an (CN); Yong-Yao Wang, Xi'an (CN); Cai-Yue Zhu, Xi'an (CN); Zhen Wang, Xi'an (CN); Jing Lou, Xi'an (CN); Qing-Qing Ma, Xi'an (CN); Yu-Xia Zhang, Xi'an (CN); Qing-Lin Jiang, Xi'an (CN); Xiao-Hong Xu, Xi'an (CN); Ting-Hua Zhang, Xi'an (CN); Jian-Gang Long, Xi'an (CN)

(73) Assignee: XI'AN JIAOTONG UNIVERSITY, Xi'an (CN)

( * ) Notice: Subject to any disclaimer, the term of this patent is extended or adjusted under 35 U.S.C. 154(b) by 0 days.

(21) Appl. No.: 16/583,263

(22) Filed: Sep. 26, 2019

(65) Prior Publication Data
US 2021/0047262 A1    Feb. 18, 2021

(30) Foreign Application Priority Data
Aug. 14, 2019    (CN) .......................... 201910746807.2

(51) Int. Cl.
*C07C 69/30*    (2006.01)
*A61P 9/10*    (2006.01)

(52) U.S. Cl.
CPC ............... *C07C 69/30* (2013.01); *A61P 9/10* (2018.01)

(58) Field of Classification Search
CPC ...................................................... C07C 69/30
See application file for complete search history.

(56) References Cited

U.S. PATENT DOCUMENTS

2003/0225160 A1* 12/2003 Geerlings ................. A61P 1/16
514/549

FOREIGN PATENT DOCUMENTS

CN    106905159 A  *  6/2017

* cited by examiner

*Primary Examiner* — Valerie Rodriguez-Garcia

(57) ABSTRACT

The disclosure relates to a compound, 2-(3,4-dihydroxyphenyl)ethyl 3-hydroxybutanoate, for improving aortic endothelial cell function and use thereof. The compound is capable of inhibiting inflammatory response of the human aortic endothelial cells caused by a saturated fatty acid, and preventing an occurrence and progression of atherosclerosis. The compound is capable of reducing human aortic endothelial inflammation caused by a saturated fatty acid, for example, reducing the mRNA levels of interleukin-6 (IL-6), and is capable of effectively protecting the function of mitochondria in human aortic endothelium from being damaged by a saturated fatty acid, for example, increasing the expression of mitochondrial complex I.

7 Claims, 2 Drawing Sheets
Specification includes a Sequence Listing.

2-(3,4-DIHYDROXYPHENYL)ETHYL 3-HYDROXYBUTANOATE, COMPOSITION, AND METHOD FOR IMPROVING FUNCTION OF AORTIC ENDOTHELIAL CELL

SEQUENCE LISTING

This application contains a Sequence Listing in computer readable form. The computer readable form is incorporated herein by reference.

CROSS-REFERENCE TO RELATED APPLICATION

This application claims all benefits accruing under 35 U.S.C. § 119 from China Patent Application No. 201910746807.2, filed on Aug. 14, 2019 in the China National Intellectual Property Administration, the content of which is hereby incorporated by reference.

FIELD

The present disclosure belongs to the pharmaceutical field, and particularly relates to 2-(3,4-dihydroxyphenyl) ethyl 3-hydroxybutanoate, a pharmaceutical composition including 2-(3,4-dihydroxyphenyl)ethyl 3-hydroxybutanoate, and a method for improving aortic endothelial cell function.

BACKGROUND

Statistical data released by World Health Organization (WHO) in 2011 shows that deaths caused by cardiovascular diseases account for 31% of global deaths, second only to the total of other non-communicable diseases. It is expected that the mortality caused by cardiovascular diseases will be significantly higher than other diseases from 2008 to 2030, taking the lead position. The pathological basis of cardiovascular diseases and cerebrovascular diseases, such as myocardial infarction and cerebral infarction, is atherosclerosis.

Atherosclerosis, whose pathogenesis is very complex, is a chronic inflammatory response with plaques inside arteries, and accompanied by damages to vascular endothelial cells. The main factors leading to atherosclerosis are an unhealthy diet such as high-salt, high-fat, and high-energy diet, smoking, and metabolic risk factors, including diseases such as "Three-High" symptom (hypertension, hyperglycemia, and hyperlipidemia) and obesity.

Although atherosclerosis may be treated by medicine or surgery, it is latent leading to a high lethality rate and a high disability rate. Therefore, prevention and early treatment of atherosclerosis are particularly favorable. Studies have revealed that natural active ingredients such as chlorogenic acid, "Xiongshao" (*Ligusticum chuanxiong* and *Paeoniae rubra radix*) and lignans have anti-atherosclerotic effects, and functional foods containing these ingredients are available on the market. It is of great significance and prospect to explore new substances that are effective against cardiovascular diseases such as atherosclerosis.

SUMMARY

The present disclosure provides a compound, 2-(3,4-dihydroxyphenyl)ethyl 3-hydroxybutanoate, a pharmaceutical composition containing the compound, and a method for improving aortic endothelial cell function.

2-(3,4-dihydroxyphenyl)ethyl 3-hydroxybutanoate is found to significantly inhibit inflammatory response of human aortic endothelial cells induced by a saturated fatty acid, and increase a production of mitochondrial complex in vascular endothelial cells, preventing the occurrence and development of atherosclerosis by anti-inflammatory and protecting mitochondrial function.

The present disclosure provides the compound, 2-(3,4-dihydroxyphenyl)ethyl 3-hydroxybutanoate that is represented by a chemical formula I.

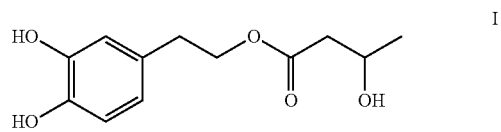 [SMILES: CC(O)CC(=O)OCCc1ccc(O)c(O)c1]

2-(3,4-dihydroxyphenyl)ethyl 3-hydroxybutanoate has an inhibitory effect on an inflammation of aortic endothelial cells caused by a saturated fatty acid.

2-(3,4-dihydroxyphenyl)ethyl 3-hydroxybutanoate is capable of reducing a mRNA level corresponding to interleukin-6 (IL-6) in aortic endothelial cells.

2-(3,4-dihydroxyphenyl)ethyl 3-hydroxybutanoate is capable of protecting mitochondria from being damaged by inflammation of aortic endothelial cells caused by a saturated fatty acid.

2-(3,4-dihydroxyphenyl)ethyl 3-hydroxybutanoate is capable of increasing an expression of mitochondrial complex I protein.

2-(3,4-dihydroxyphenyl)ethyl 3-hydroxybutanoate is capable of being used in preparing a pharmaceutical composition for improving aortic endothelial cell function.

2-(3,4-dihydroxyphenyl)ethyl 3-hydroxybutanoate is capable of being used in preparing a pharmaceutical composition for preventing or treating a cardiovascular disease.

2-(3,4-dihydroxyphenyl)ethyl 3-hydroxybutanoate is capable of being used in preparing a pharmaceutical composition for preventing atherosclerosis.

The present disclosure provides the pharmaceutical composition that includes 2-(3,4-dihydroxyphenyl)ethyl 3-hydroxybutanoate.

The present disclosure provides use of 2-(3,4-dihydroxyphenyl)ethyl 3-hydroxybutanoate in preparing the pharmaceutical composition for improving aortic endothelial cell function.

The present disclosure provides use of 2-(3,4-dihydroxyphenyl)ethyl 3-hydroxybutanoate in preparing the pharmaceutical composition for preventing or treating a cardiovascular disease.

The present disclosure provides use of 2-(3,4-dihydroxyphenyl)ethyl 3-hydroxybutanoate in preparing the pharmaceutical composition for preventing atherosclerosis.

The pharmaceutical composition can further include a pharmaceutical acceptable diluent, excipient, or carrier.

The pharmaceutical composition can be medicine or nutritional supplement that includes 2-(3,4-dihydroxyphenyl)ethyl 3-hydroxybutanoate.

The present disclosure provides a method for improving function of an aortic endothelial cell, the method includes contacting the cell with an effective amount of 2-(3,4-dihydroxyphenyl)ethyl 3-hydroxybutanoate.

The present disclosure provides a method for inhibiting saturated fatty acid induced inflammation of an aortic endothelial cell, the method includes contacting the cell with an effective amount of 2-(3,4-dihydroxyphenyl)ethyl 3-hydroxybutanoate.

The present disclosure provides a method for reducing a mRNA level corresponding to interleukin-6 (IL-6) in an aortic endothelial cell, the method includes contacting the cell with an effective amount of 2-(3,4-dihydroxyphenyl)ethyl 3-hydroxybutanoate.

The present disclosure provides a method for protecting a mitochondrion from being damaged by saturated fatty acid induced inflammation of an aortic endothelial cell, the method includes contacting the cell with an effective amount of 2-(3,4-dihydroxyphenyl)ethyl 3-hydroxybutanoate.

The present disclosure provides a method for increasing an expression of mitochondrial complex I protein in an aortic endothelial cell, the method includes contacting the cell with an effective amount of 2-(3,4-dihydroxyphenyl)ethyl 3-hydroxybutanoate.

The present disclosure provides a method for preventing or treating a cardiovascular disease, the method includes administering to a patient in need thereof a therapeutically effective amount of 2-(3,4-dihydroxyphenyl)ethyl 3-hydroxybutanoate.

The present disclosure provides a method for preventing atherosclerosis, the method includes administering to a patient in need thereof a therapeutically effective amount of 2-(3,4-dihydroxyphenyl)ethyl 3-hydroxybutanoate.

The 2-(3,4-dihydroxyphenyl)ethyl 3-hydroxybutanoate is capable of increasing a cell viability of human aortic endothelial cells. The 2-(3,4-dihydroxyphenyl)ethyl 3-hydroxybutanoate can significantly inhibit the inflammatory response of human aortic endothelial cells induced by a saturated fatty acid and increase the production of a mitochondrial complex in vascular endothelial cells, in vascular diseases such as atherosclerosis, that has a damage or inflammation of vascular endothelium. The 2-(3,4-dihydroxyphenyl)ethyl 3-hydroxybutanoate prevents the occurrence and development of atherosclerosis by anti-inflammation and protecting the mitochondria.

The 2-(3,4-dihydroxyphenyl)ethyl 3-hydroxybutanoate is capable of effectively reducing human aortic endothelial inflammation caused by a saturated fatty acid, for example, reducing a level of mRNAs corresponding to interleukin-6 (IL-6). The 2-(3,4-dihydroxyphenyl)ethyl 3-hydroxybutanoate is capable of effectively protecting the function of the mitochondria in human aortic endothelial cells from being damaged by a saturated fatty acid, for example, increasing an expression of mitochondrial complex I protein. The 2-(3,4-dihydroxyphenyl)ethyl 3-hydroxybutanoate, the pharmaceutical composition, the medicine, and the nutritional supplement have a good application prospect in preventing the occurrence and development of vascular diseases.

BRIEF DESCRIPTION OF THE DRAWINGS

Implementations are described by way of example only with reference to the attached figures.

FIG. 3A and FIG. 3B are diagrams showing that HT-HB is capable of avoiding a palmitic acid-induced decrease of mitochondrial complex I expression in human aortic endothelial cells, wherein FIG. 3A shows a Western blot testing result, FIG. 3B is a statistical diagram based on the Western blot testing result, the abscissa of FIG. 3B represents the protein name, and the ordinate of FIG. 3B represents relative protein expression level.

DETAILED DESCRIPTION

Figure 1:
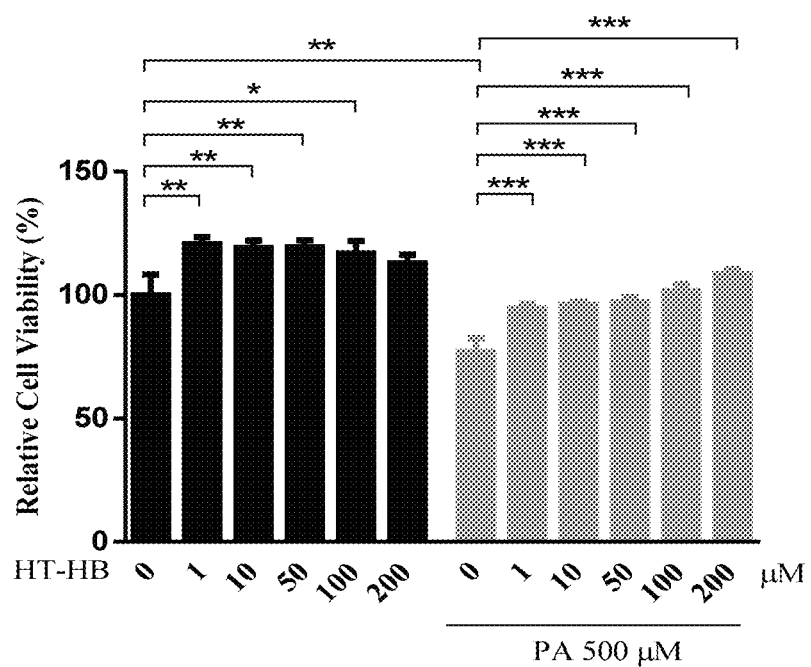
FIG. 1 is a diagram showing a protective effect of 2-(3,4-dihydroxyphenyl)ethyl 3-hydroxybutanoate (HT-HB) in different concentrations on cell viability of human aortic endothelial cells, wherein the abscissa represents the concentration of HT-HB, and the ordinate represents relative cell viability.

A detailed description with the above drawings is made to further illustrate the present disclosure.

1. Experimental Materials

The present disclosure relates to a compound, 2-(3,4-dihydroxyphenyl)ethyl 3-hydroxybutanoate (HT-HB), having a chemical structure represented by formula I.

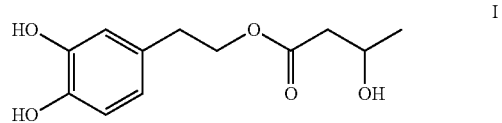 [SMILES: CC(O)CC(=O)OCCc1ccc(O)c(O)c1]

In an embodiment, the compound can be synthesized as the following scheme.

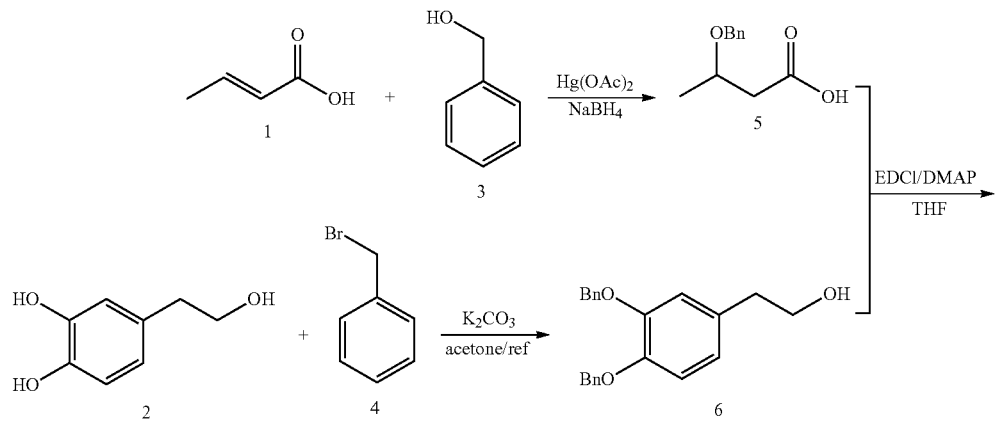

-continued

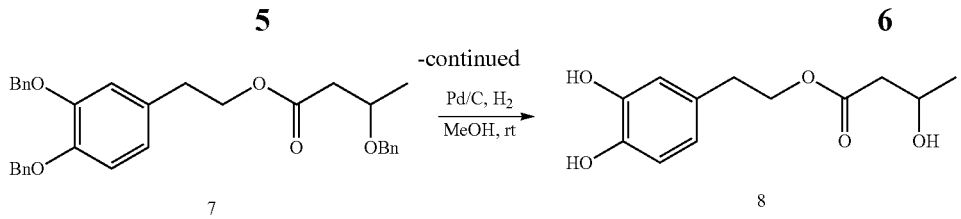

Crotonic acid (1) (2.55 g, 29.7 mmol) was weighed in a 150 ml round bottom flask, added with benzyl alcohol (3) (30 ml) and mercuric acetate (9.63 g, 30 mmol) in sequence. The mixture was stirred at room temperature overnight. Then, the flask was placed in a low-temperature condensation tank and cooled to 0° C. 30 ml of sodium hydroxide (3N purity) was added in the flask within 5 to 10 minutes, and then 30 ml of sodium hydroxide (3N purity) water solution containing 0.5 M (0.57 g) of sodium borohydride (NaBH$_4$) was added in the flask. Then, the mixture was kept at 0° C. for 3 to 10 minutes. After that, the mixture was taken out and stirred at room temperature for 1 to 2 hours, followed with a filtration to obtain a filtrated liquid, which was extracted 3 to 4 times with 75 mL of diethyl ether to remove excess benzyl alcohol (3). The filtrated liquid was then acidified to pH=2 by using 10% hydrochloric acid, and a large amount of white solid was precipitated, which was filtered out to obtain β-benzyloxybutyric acid (5) as the white solid, 4.32 g, yield 75%. $^1$H NMR (400 MHz, CDCl3) δ 7.40-7.28 (m, 5H), 4.58 (dd, J=33.0, 11.6 Hz, 2H), 4.30-4.19 (m, 1H), 3.93-3.18 (m, 1H), 3.55 (d, J=5.5 Hz, 1H), 1.44 (d, J=5.9 Hz, 3H).

3,4-dihydroxyphenylethanol (2) (1 g, 6.49 mmol) and potassium carbonate (3.59 g, 25.9 mmol) were mixed in a 50 ml round bottom flask, added with anhydrous acetone (20 ml) to dissolve, and then added with benzyl bromide (4) (1.62 ml, 13.62 mmol). The mixture was stirred at 70° C. for 4 to 5 hours until the reaction was indicated as completed by thin layer chromatography (TLC). The product was filtered to remove the potassium carbonate, concentrated, and then applied to column chromatography (DCM:EA=20:1) to obtain 4-dibenzyloxyphenylethanol (6), white solid, 1.86 g, yield 86%. $^1$H NMR (400 MHz, CDCl3) δ 7.45-7.43 (m, 4H), 7.39-7.26 (m, 6H), 6.88 d, J=8.1 Hz, 1H), 6.81 (d, J=2.0 Hz, 1H), 6.73 (dd, J=8.1, 2.0 Hz, 1H), 5.15 (s, 2H), 5.13 (s, 2H), 3.77 (q, J=6.3 Hz, 2H), 2.75 (t, J=6.4 Hz, 2H).

β-benzyloxybutyric acid (5) (1.24 g, 6.4 mmol) in a 100 ml round bottom flask was added with THF (45 ml), 3,4-dibenzyloxyphenylethanol (6) (1.34 g, 4 mmol), EDCI (1.53 g, 8 mmol), and DMAP (50 mg) in sequence, stirred in an oil bath at 30° C. for 3 to 4 hours until 3-benzyloxybutyric acid was indicated as disappeared by TLC, and the reaction was stopped. The production was concentrated, added with EA to dissolve and wash 2 to 3 times, concentrated and then applied to column chromatography (PE:DCM=1:1) to obtain 3-benzyloxy-3',4'-dibenzyloxy-phenethyl butyrate (7), which is a pink oil, 823 mg, yield 40%. $^1$H NMR (400 MHz, CDCl3) δ 7.47-7.39 (m, 4H), 7.38-7.26 (m, 10H), 7.25-7.23 (m, 1H), 6.85 (d, J=8.2 Hz, 1H), 6.80 (d, J=1.9 Hz, 1H), 6.71 (dd, J=8.2, 2.0 Hz, 1H), 5.12 (s, 2H), 5.11 (s, 2H), 4.49 (dd, J=33.0, 11.6 Hz, 2H), 4.28-4.17 (m, 2H), 4.02-3.92 (m, 1H), 2.81 (t, J=7.1 Hz, 2H), 2.61 (dd, J=15.0, 7.3 Hz, 1H), 2.39 (dd, J=15.0, 5.7 Hz, 1H), 1.22 (d, J=6.2 Hz, 3H).

3-benzyloxy-3',4'-dibenzyloxy-phenethyl butyrate (7) (2 g, 3.92 mmol) was dissolved in anhydrous methanol (40 ml) in a 100 ml round bottom flask, then added with 10% Pd/C (200 mg), stirred at room temperature in hydrogen atmosphere (pressure of hydrogen gas is 1 atmospheric pressure) for 16 hours, filtered, concentrated, and purified by column chromatography (DCM:MeOH=80:1) to obtain 2-(3,4-dihydroxyphenyl)ethyl 3-hydroxybutanoate (8), which is a colorless or pale yellow oil, 762 mg, yield 80%. $^1$H NMR (400 MHz, CDCl3) δ 6.76 (d, J=8.0 Hz, 1H), 6.70 (d, J=1.8 Hz, 1H), 6.69-6.51 (m, 2H), 6.33 (s, 1H), 4.32-4.23 (m, 2H), 4.23-4.14 (m, 1H), 3.42 (s, 1H), 2.79 (t, J=6.8 Hz, 2H), 2.48-2.37 (m, 2H), 1.20 (d, J=6.3 Hz, 3H). 13C NMR (101 MHz, CDCl3) δ 172.88, 143.92, 142.69, 130.17, 121.04, 115.95, 115.52, 65.51, 64.71, 42.89, 34.25, 22.31. HRMS (ESI): calculated for $C_{12}H_{16}NaO_5^+[M+Na]^+$, 263.0890; found 263.0891.

HT-HB solutions with different concentrations, 0 μmol/L (μM), 1 μM, 10 μM, 50 μM, 100 μM, and 200 μM, were prepared by dissolving HT-HB in water.

TRIzol™ reagent was purchased from Invitrogen™. RNA reverse transcription kit and SYBR fluorescent dye were purchased from Takara Biotechnology (Dalian) Co., Ltd. RNA primers were ordered from and synthesized by Xi'an Qingkezexi Bio Co., Ltd.

2. Culture of Experimental Cells and Model Establishment

Human aortic endothelial cells (HAECs) were purchased from Shanghai Shanghai Bioleaf Biotech Co., Ltd. Palmitic acid (PA) was purchased from SIGMA Company. A palmitic acid solution having a concentration of 500 μM was prepared by dissolving palmitic acid in water. A cell culture incubator was adopted to culture the cells in a temperature-constant, humidified, sterile condition. The cells were cultured in wells of culture plates at an atmosphere of 95% air and 5% $CO_2$ at 37° C. in the incubator. The experiments were performed on different experimental groups of cells.

3. Experimental Methods (1) MTT (3-(4,5-Dimethylthiazol-2-yl)-2,5-diphenyltetrazolium Bromide) Assay The HAECs that were previously cultured in a 12-well cell culture plates were divided into 6 different experimental groups and respectively applied with HT-HB in different concentrations, 0 μM, 1 μM, 10 μM, 50 μM, 100 μM, and 200 μM, all followed with an 24-hour incubation. Then, each of the 6 groups of cells was further divided into two sub groups, one was applied with 500 μM palmitic acid, the other was not, all followed with another 24-hour incubation.

An MTT assay was performed to all groups of cells. The MTT assay was a laboratory test and standard colorimetric assay for measuring the activity of enzymes that reduced MTT to formazan, giving a purple colour. Yellow MTT was reduced to purple formazan in living cells. For each group, HAECs were washed with phosphate-buffered saline (PBS) once, applied with 0.5 mg/ml of MTT, and cultured in the incubator containing 95% air and 5% $CO_2$ at 37° C. for 4 hours. The cultured cells were then washed three times with PBS before adding dimethyl sulfoxide (DMSO) to turn the insoluble purple formazan product into a colored solution. The absorbance was measured at a wavelength of 490 nm in a spectrophotometer. The absorbance of this colored solution can be quantified by measuring at a certain wavelength (usually between 500 and 600 nm) by a spectrophotometer.

(2) IL-6 mRNA Level Detection

The HAECs that were previously cultured in a 12-well cell culture plate were divided into 4 different experimental groups and respectively applied with HT-HB in different concentrations, 0 μM, 0 μM, 50 μM, 100 μM, all followed with an 24-hour incubation. Then, the last 3 groups of cells were respectively applied with 500 μM palmitic acid, the first was not, all followed with another 24-hour incubation. The detecting of mRNA levels corresponding to interleukin-6 (IL-6) was respectively carried out on each group of cells by using reverse transcription RNA and real-time quantitative polymerase chain reaction (PCR), and the specific method is as follows:

1) RNA Extraction

The medium for cell culture in the wells was removed. 500 μL of TRIzol™ reagent was added to each well, and the culture plate was then shaken at room temperature for 5 minutes. Then the cells in the wells were collected and transferred to a 1.5 mL eppendorf (EP) tube. 200 μl (taking ⅕ of total volume of the substance in the EP tube) of chloroform was then added to the EP tube for extraction of protein. The samples were then vigorously stirred for 15 seconds, rested for 15 minutes at room temperature, and then centrifuged at a relative centrifugal force of 12,000 g for 10 minutes at 4° C. The upper aqueous phase of each sample was transferred to another new EP tube, to which isopropanol with a volume equal to the transferred upper aqueous phase was added and uniformly mixed with the transferred upper aqueous phase. The solution rested for 1 hour at −20° C., and then centrifuged at 12,000 g for 10 minutes at 4° C. The supernatant was discarded, and 1 mL of pre-cooled 75% ethanol was added to the RNA pellet and mixed by pipetting up and down. The solution was centrifuged at 12,000 g for 10 minutes at 4° C., and then the supernatant is discarded. The EP tube containing the RNA pellet was placed on a super-clean bench for 30 minutes to completely evaporate the ethanol, and the resultant was resuspended in 10 μL of DEPC-treated water to form a total RNA solution for the following reverse transcription. The concentration of the solution was measured by an ultraviolet spectrophotometer.

2) Reverse Transcription of RNA

For performing the reverse transcription, a solution with a total volume of 20 μl was prepared by mixing 2 μg of the extracted RNA, 0.5 μg of random primers, 4 μL of 5× Master Mix, and DEPC-treated water taking all the rest volume. The solution was incubated at 37° C. for 60 minutes to have the reverse transcription reaction to obtain cDNA, then inactivated at 80° C. for 15 seconds, and then stored at −20° C. for later use.

3) Real-Time Quantitative PCR (RT-PCR)

RT-PCR was performed by using the RNA reverse transcription kit and the SYBR fluorescent dye. A system with a total volume of 10 μL was prepared by mixing 1 μL of the obtained cDNA, 5 μL of 2×SYBP®Premix Ex Taq™ II, 0.5 μL of a mixture of forward primer and backward primer (10 μM), and sterilized water taking all the rest volume. The RT-PCR was performed according to instructions of the kit with a protocol as follows: unwinding at 95° C. for 10 minutes; performing PCR for 40 cycles, each of which was performed by sequentially subjecting the system at 95° C. for 30 seconds, at 55° C. for 30 seconds, and at 72° C. for 20 seconds; and finally observing and analyzing a dissociation curve performed by sequentially subjecting the system at 95° C. for 15 seconds, at 60° C. for 15 seconds, and at 95° C. for 15 seconds). β-actin was used as an internal reference, the primer sequences used in the experiment were as follows:

PCR primers for IL-6:
Forward primer: 5'-TTTTGTACTCATCTGCACAGC-3' (SEQ ID NO: 1)
Backward primer: 5'-GGATTCAATGAGGAGACTTGC-3' (SEQ ID NO: 2)
PCR primers for β-actin:
Forward primer: 5'-ATCATGTTTGAGACCTTCAA-3' (SEQ ID NO: 3)
Backward primer: 5'-AGATGGGCACAGTGTGGGT-3' (SEQ ID NO: 4)

(2) Protein Detection

The HAECs that were previously cultured in a 6-well cell culture plate were divided into 3 different experimental groups, the control (Ctrl) group, the PA group, and the HT-HB+PA group. The cells of the HT-HB+PA group were applied with HT-HB in a concentration of 100 μM followed with an 24-hour incubation. Then, the cells of both the PA group and the HT-HB+PA group were applied with 500 μM palmitic acid, all followed with another 24-hour incubation. The protein detection was respectively carried out on each group of cells as follows.

1) Protein Extraction

The medium for cell culture in the wells was removed. 150 μL of IP lysis buffer was added to each well of the culture plat. The cultured cells in the wells were scraped by using a cell scraper, collected and transferred to a 1.5 mL EP tube, and subjected to vibrating for 15 seconds and cooling in ice bath for 10 minutes. The vibrating and cooling were repeated three times, ensuring that the cells were ice bathed for at least 30 minutes. Then, the samples were centrifuged at 12,000 g for 10 minutes at 4° C. The supernatants were collected, and the proteins therein were quantified by bicinchoninic acid (BCA) assay, and normalized. Then, the supernatants were added with 5× loading buffer and mercaptoethanol, and boiled for 10 minutes to denature the proteins. The extracted proteins were stored at −80° C. for later use.

2) Western Blot

10 μg of the extracted proteins were subjected to gel electrophoresis with 10% acrylamide gel, and electrophoretic transferred onto a PVDF membrane, which were blocked, and incubated with a primary antibody at 4° C. overnight, free primary antibody was washed away. Then, the membrane was incubated with a secondary antibody at room temperature for 1 hour, and free secondary antibody was washed away. Target proteins were detected by chemiluminescence.

4. Statistical Analysis

Figure 2:
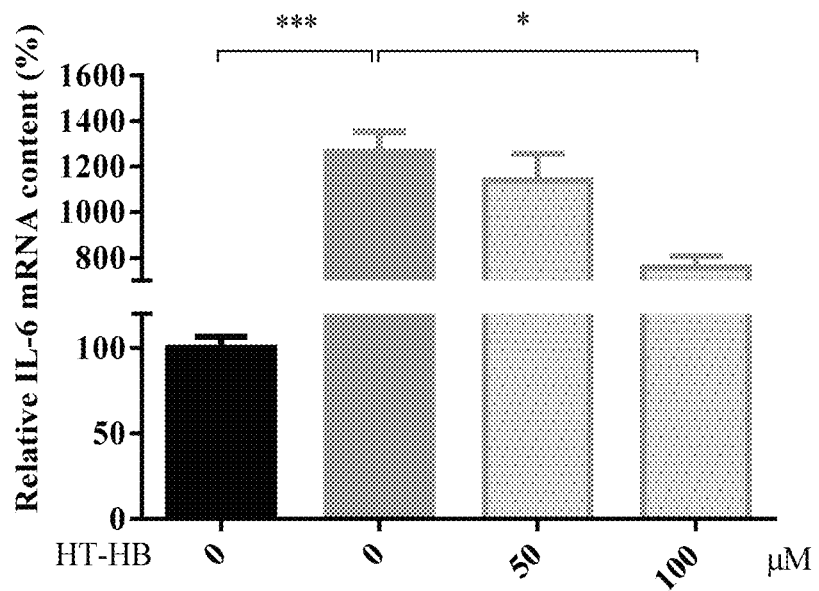
FIG. 2 is a diagram showing the inhibitory effect of an embodiment of HT-HB in different concentrations on palmitic acid-induced inflammation of human aortic endothelial cells, wherein the abscissa represents the concentration of HT-HB, and the ordinate represents mRNA level corresponding to IL-6.
Figure 3A:
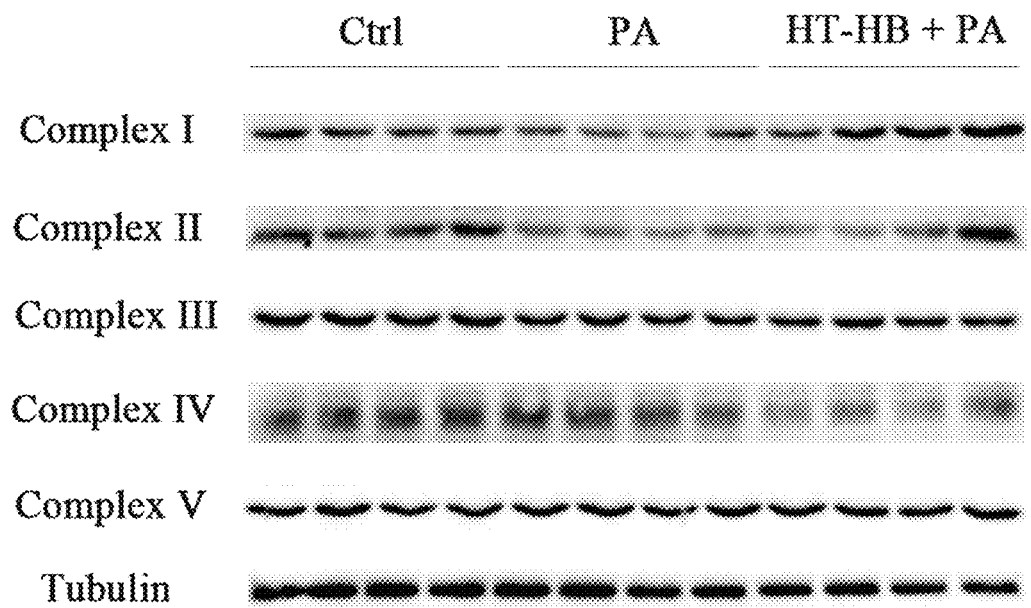
Figure 3B:
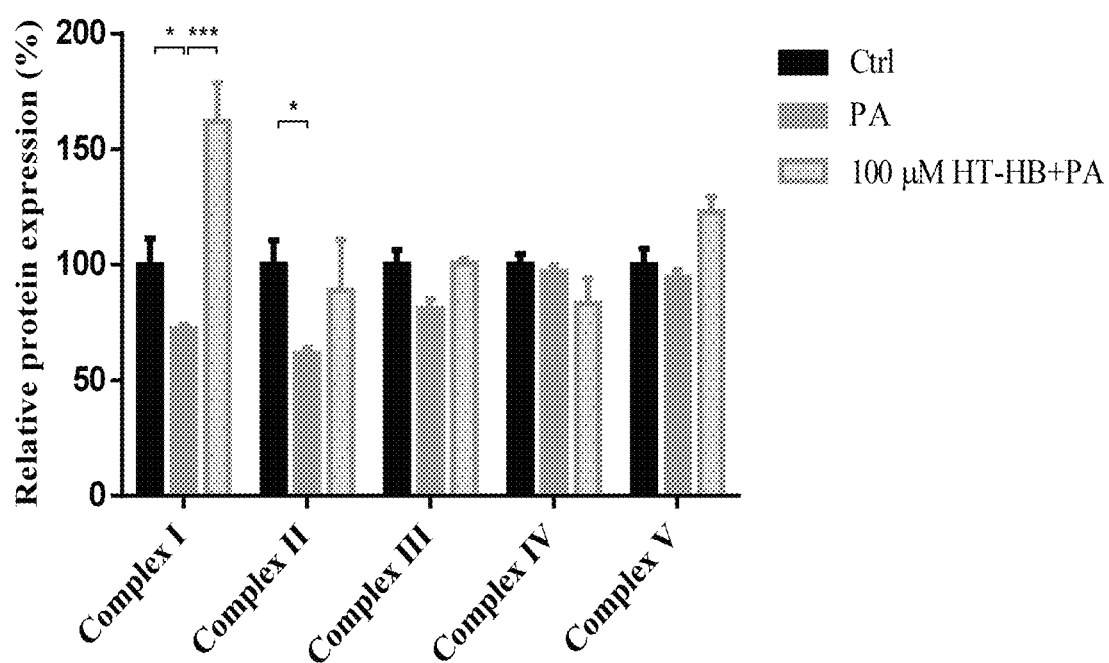

Referring to FIG. 1, FIG. 2, and FIG. 3B, the data obtained in the above-described experiments were expressed in the diagrams in form of mean±SEM (SEM is standard error of mean), and the data were analyzed by using Oneway ANOVA analysis method with statistical significance p values of * meaning $p<0.05$,  meaning $p<0.01$, * meaning $p<0.001$.

5. Viability Increase of HAECs and Viability Increase of HAECs Inhibited by Palmitic Acid Referring to FIG. 1, the left set of data (in black) corresponds to the cells that were not treated with palmitic acid, and the right set of data (in grey) corresponds to the cells that were treated with palmitic acid. It can be seen from the left set of data that the cells that were treated with the HT-HB in the concentration of 1 µM to 100 µM show higher viabilities than the cells without the HT-HB treatment (the control group), revealing that HT-HB in the concentration of 1 µM to 100 µM is capable of increasing the viability of human aortic endothelial cells. It can be seen from the right set of date that the palmitic acid treated cells which were previously treated with HT-HB in the concentration of 1 µM to 100 µM show higher viabilities than the palmitic acid treated cells without the HT-HB treatment, revealing that HT-HB is also capable of increasing the viability of the palmitic acid inhibited cells. A concentration dependency of the viability can be seen that the higher the concentrations of HT-HB, the higher the cell viability of the palmitic acid inhibited cells.

6. Inhibitory Effect of HT-HB on Palmitic Acid-Induced Inflammation of Human Blood Aortic Endothelial Cells HT-HB is capable of significantly inhibiting the inflammatory response caused by palmitic acid induced damage to the human vascular endothelial cells. Referring to FIG. 2, from left to right along the abscissa, the first data (in black) corresponds to the cells of the control group, the second data (in darker grey) corresponds to the cells that were treated with palmitic acid without the HT-HB treatment, the third and fourth data (in lighter grey) corresponds to the cells that were previously treated with HT-HB in different concentrations and then treated with palmitic acid. 500 µM of palmitic acid induced an inflammatory response in human aortic endothelial cells. As shown in FIG. 2, the cellular inflammatory factor, interleukin (IL-6), was significantly higher in palmitic acid treated cells than that in the control group. The mRNA level corresponding to IL-6 was increased for about 10 times, revealing that the level of inflammation in the 500 µM palmitic acid treatment group, was increased significantly. It can be seen from FIG. 2 that by applying HT-HB with the concentration of 100 µM, the mRNA level corresponding to IL-6 was significantly decreased, revealing a significant inhibition of the inflammatory response. The inhibition effect increases with the concentration of HT-HB. HT-HB was thereby indicated to have an anti-inflammation effect and an anti-atherosclerosis effect.

7. Up-Regulating Effect of HT-HB on a Palmitic Acid-Induced Decrease of Expression of Mitochondrial Complex I in Human Aortic Endothelial Cells Mitochondrial respiratory chain enzyme is also called as mitochondrial respiratory chain complex or mitochondrial respiratory chain complex enzyme. The mitochondrial respiratory chain is located at inner mitochondrial membrane and composed of 5 complexes, NADH (also called as complex I), succinate dehydrogenase (also called as complex II), cytochrome C oxidoreductase (also called as complex III), cytochrome C oxidase (also called complex IV), and ATP synthase (also called as complex V). Mitochondrial complexes are closely related to electron transport and energy production. A decrease of the expression level of the complexes indicates a deterioration of the mitochondrial function of the cells. FIG. 3A and FIG. 3B show that palmitic acid is capable of reducing the expression of mitochondrial complexes I and II in human aortic endothelial cells, while HT-HB is capable of significantly increasing the expression of mitochondrial complex I, thereby improving the mitochondrial function of the cells.

The above experimental results demonstrate that HT-HB is capable of effectively inhibiting the inflammatory response and mitochondrial damage of human aortic endothelial cells induced by high fat, thereby improving the function of human aortic endothelial cells.

HT-HB can be used in preparing a pharmaceutical composition, such as a medicine or a drug, for improving aortic endothelial cell function.

In some embodiments, the pharmaceutical composition inhibits the inflammatory response of aortic endothelial cells caused by a saturated fatty acid.

In some embodiments, the pharmaceutical composition reduces the mRNA level of IL-6 in aortic endothelial cells.

In some embodiments, the pharmaceutical composition protects mitochondria from being damaged by inflammation of aortic endothelial cells caused by a saturated fatty acid.

In some embodiments, the pharmaceutical composition increases the expression of mitochondrial complex I protein.

A dysfunction of endothelial cell is the initial characterization, the reason, and the basis of occurrence and development of atherosclerosis which is a chronic inflammatory response. The occurrence of the inflammatory response is an important cause of atherosclerosis. Meanwhile, it is reported that a damage of the mitochondria may also be one important cause of atherosclerosis since the damage may induce an energy deficiency and function deterioration of endothelial cells. HT-HB provided in the present disclosure exhibits excellent properties in protecting endothelial cells from inflammation and protecting mitochondria from being damaged in the endothelial cell damage test. Therefore, the composition provided in the present disclosure has a good prospect in prevention of cardiovascular diseases, such as atherosclerosis, that has an endothelial damage caused by high fat. HT-HB provides a new medical approach for treatment of cardiovascular diseases caused by imbalance of dietary.

In some embodiments, HT-HB provided in the present disclosure can be used in preparing a medicine or a nutritional supplement for prevention or treatment of cardiovascular diseases.

In some embodiments, HT-HB provided in the present disclosure can be used in preparing a medicine or a nutritional supplement for prevention or treatment of atherosclerosis.

Finally, it is to be understood that the above-described embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

What is claimed is:

1. A compound, 2-(3,4-dihydroxyphenyl)ethyl 3-hydroxybutanoate.

2. A method for improving function of an aortic endothelial cell, the method comprising contacting the cell with an effective amount of the compound of claim 1.

3. A method for inhibiting saturated fatty acid induced inflammation of an aortic endothelial cell, the method comprising contacting the cell with an effective amount of the compound of claim 1.

4. A method for reducing a mRNA level corresponding to interleukin-6 (IL-6) in an aortic endothelial cell, the method comprising contacting the cell with an effective amount of the compound of claim 1.

5. A method for protecting a mitochondrion from being damaged by saturated fatty acid induced inflammation of an aortic endothelial cell, the method comprising contacting the cell with an effective amount of the compound of claim 1.

6. A method for increasing an expression of mitochondrial complex I protein in an aortic endothelial cell, the method comprising contacting the cell with an effective amount of the compound of claim 1.

7. A method for preventing atherosclerosis, the method comprising administering to a patient in need thereof a therapeutically effective amount of the compound of claim 1.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Forward primer for IL-6

<400> SEQUENCE: 1
ttttgtactc atctgcacag c                                               21

<210> SEQ ID NO 2
<211> LENGTH: 21
<212> TYPE: DNA
<213> ORGANISM: Artificial Sequence
<220> FEATURE:
<223> OTHER INFORMATION: Backward primer for IL-6

<400> SEQUENCE: 2
ggattcaatg aggagacttg c                                               21

<210> SEQ ID NO 3
<211> LENGTH: 20
<212> TYPE: DNA
<213> ORGANISM: Artificial Sequence
<220> FEATURE:
<223> OTHER INFORMATION: Forward primer for beta-actin

<400> SEQUENCE: 3
atcatgtttg agaccttcaa                                                 20

<210> SEQ ID NO 4
<211> LENGTH: 19
<212> TYPE: DNA
<213> ORGANISM: Artificial Sequence
<220> FEATURE:
<223> OTHER INFORMATION: Backward primer for beta-actin

<400> SEQUENCE: 4
agatgggcac agtgtgggt                                                  19